(12) United States Patent
Yang et al.

(10) Patent No.: US 10,425,063 B2
(45) Date of Patent: Sep. 24, 2019

(54) BAND-PASS FILTER

(71) Applicant: UNIVERSITÄT ZÜRICH, Zürich (CH)

(72) Inventors: Minhao Yang, New York, NY (US); Shih-Chii Liu, Zürich (CH)

(73) Assignee: UNIVERSITÄT ZÜRICH, Zürich (CH)

( * ) Notice: Subject to any disclaimer, the term of this patent is extended or adjusted under 35 U.S.C. 154(b) by 0 days.

(21) Appl. No.: 16/069,872

(22) PCT Filed: Jan. 5, 2017

(86) PCT No.: PCT/EP2017/050231
§ 371 (c)(1),
(2) Date: Jul. 12, 2018

(87) PCT Pub. No.: WO2017/121682
PCT Pub. Date: Jul. 20, 2017

(65) Prior Publication Data
US 2019/0020331 A1 Jan. 17, 2019

(30) Foreign Application Priority Data
Jan. 13, 2016 (EP) ..................... 16151107

(51) Int. Cl.
H03K 21/00 (2006.01)
H03K 5/24 (2006.01)
(Continued)

(52) U.S. Cl.
CPC .......... H03H 21/0016 (2013.01); A61F 2/18 (2013.01); H03H 11/1213 (2013.01); H03K 5/24 (2013.01);
(Continued)

(58) Field of Classification Search
CPC combination set(s) only.
See application file for complete search history.

(56) References Cited

U.S. PATENT DOCUMENTS 5,311,457 A * 5/1994 Shizawa ............ H03H 17/0292
708/316
7,898,243 B2 * 3/2011 Werner .................. G01R 33/02
324/207.22
(Continued)

FOREIGN PATENT DOCUMENTS

JP  2010-93560 A  4/2010
WO 2007/034222 A2  3/2007

OTHER PUBLICATIONS

Chen, Y., et al., "0.07 nm2, 2 mW, 75 MHz-IF,fourth-order BPF using source-follower-based resonator in 90 nm CMOS", Electronics Letters, IEE Stevenage, GB, vol. 48, Issue 10, pp. 553-554 (May 10, 2012).

(Continued)

Primary Examiner — An T Luu
(74) Attorney, Agent, or Firm — Maschoff Brennan

(57) ABSTRACT

A band-pass filter is described comprising a first first-order filter stage comprising a first resistor characterized by a first impedance and connected to a first node, referred to as a filter input node, and, through a second node to a first reactive component connected to a third node, the first impedance being such that a first current therethrough is dependent on the difference between the voltages at the first and second nodes; and a second first-order filter stage comprising a second resistor characterized by a second impedance and connected to the second node, and, through a fourth node, to a second reactive component connected to a fifth node. The second impedance is such that a second current therethrough is dependent on the negative of the sum of the voltages at the second and fourth nodes. The band- (Continued)

pass filter further comprises summing means for summing the voltages at the second and fourth nodes to output a voltage at a sixth node.

15 Claims, 4 Drawing Sheets

(51) Int. Cl.
  *H03K 19/20* (2006.01)
  *H03H 21/00* (2006.01)
  *H03H 11/12* (2006.01)
  *A61F 2/18* (2006.01)
  *H04R 25/00* (2006.01)
  *A61F 2/48* (2006.01)
  *H03K 5/00* (2006.01)
  *H03M 3/02* (2006.01)

(52) U.S. Cl.
  CPC ............ *H03K 19/20* (2013.01); *H04R 25/505* (2013.01); *A61F 2002/183* (2013.01); *A61F 2002/482* (2013.01); *A61F 2250/0002* (2013.01); *H03K 2005/00078* (2013.01); *H03M 3/02* (2013.01); *H04R 2225/67* (2013.01)

(56) References Cited

U.S. PATENT DOCUMENTS

| 8,089,310 B2* | 1/2012 | Iida ...................... H03H 19/004 327/231 |
| 8,710,921 B2 | 4/2014 | Conta et al. |
| 2007/0004356 A1* | 1/2007 | Sessink ............... H04B 1/1081 455/222 |

OTHER PUBLICATIONS

Kitsunezuka, M., et al., "A 30MHz-2.4GHz CMOS receiver with integrated RF filter and dynamic-range-scalable energy detector for cognitive radio," Frequency Integrated Circuits Symposium, Baltimore, MD, pp. 1-4 (Jun. 2011).

Metal, Y., "14.4 nW fourth-order bandpass filter for biomedical applications", Electronic Letters, The Institution of Engineering and Technology, vol. 46, Issue 14, pp. 973-974 (Jul. 8, 2010).

* cited by examiner

BAND-PASS FILTER

TECHNICAL FIELD

The present invention relates to band-pass filter (BPF) designs to be used for example in artificial cochlea systems. The invention also relates to a data processing apparatus comprising the BPF and to a method of operating the data processing apparatus.

BACKGROUND OF THE INVENTION

Filter circuits are well known, and various different configurations are known which provide different frequency responses. Generally, a filter circuit can be categorised as any of a low-pass by which low frequency signals are passed, high-pass by which high frequency signals are passed, band-pass by which only signals within a certain frequency band are passed, or band-stop by which only signal frequencies outside a particular band are passed. Furthermore, within these classifications various other classifications can be made dependent upon the precise filter response, for example Butterworth, Chebyshev, Bessel, or the like. Such filters may be passive filters, which means that the components have no amplifying/active (either voltage or current) elements therein, or active filters, which usually comprise one or more transistors provided with a power supply to act as an active element. Various different transistor circuits are known in the art, one of which is the source follower circuit (equivalent to an emitter follower, or common collector circuit when using bipolar junction transistors). The source follower is a known basic building block for micro electronics designs, and exhibits excellent linearity. Due to this high linearity it has been proposed previously that the source follower circuit can be the basis of a high-linearity and low-power analogue filter.

Power consumption is an important factor to be considered when designing filter circuits. U.S. Pat. No. 8,710,921 discloses an example of a power-efficient and stable higher order low-pass filter. However, designing band-pass filters is typically more complex and there is currently a need for band-pass filters which have a very low power consumption, yet are stable and have a simple design.

Band-pass filters are used in various systems and fields. One such field, which is currently widely investigated, is artificial or silicon cochlea. Because human brains can process information more efficiently both in terms of power and latency even under uncontrolled conditions, increasing academic and industrial players are investigating brain-like event-driven computing methods in an attempt to mimick the brain's capability. Artificial spiking sensors such as silicon retinas and cochleas naturally provide asynchronous event-driven outputs in response to changes in the environment and are therefore a source of sensory input to processors like silicon neural networks for real-time event-driven intelligent processing. The silicon cochlea, in particular, sees wide applications in auditory sensing applications such as mobile speech control and ambient assisted living, where chip power is the major concern. To directly utilise the energy harvested from environment for powering the chip, a low power supply is also preferred.

FIG. 1 is a simplified block diagram illustrating an example of a prior art silicon cochlea system 1. In this example the on-chip cochlea comprises a core 2 powered by a power source (not shown), in this example a voltage source of 0.5 V, and a 1.8 V address event representation (AER) circuitry 3, which is a protocol for asynchronously sending generated spikes off-chip. The core further comprises binaural parallel channels 5, in this example 64 channels, and a current bias generator (CBG) 7 to provide 64 geometrically scaled currents to the corresponding channels, so that the characteristic central frequencies of the channels are geometrically scaled from 20 Hz to 20 kHz, covering the frequency range of human hearing. It is to be noted that in some cases optional gain amplifiers 9 could be included on-chip. In one channel, as shown in FIG. 2, there are left and right sub-channels receiving the audio signals from left and right microphones 10 but in general, the input signals to the sub-channels could come from other sources such as antennas or electrodes. A translinear loop (TLL) 11 is provided for quality factor (Q factor) tuning of bandpass filters. The TLL 11 is shared by the left and right sub-channels. The TLL 11, having a channel biasing functionality integrated with it, distributes all the current biases needed for the circuit blocks in one channel, which include two band-pass filters (BPFs) 13, two asynchronous delta modulators (ADMs) 15 used for analogue-to-spike conversion, and two asynchronous logic (AL) units 17, which generate control signals for the ADMs and communicate with the peripheral AER circuits. The generated spikes from all the channels are transmitted off-chip by the 1.8 V AER circuitry 3. Before the BPFs, there are programmable attenuators (PAs) 19 for attenuating large input signals.

The existing methods of building analogue band-pass filters e.g. in artificial cochlea systems are: active resistor-capacitor (active RC) filters, filters using operational transconductance amplifiers (OTAs) and more specifically OTA-capacitor (OTA-C), switched-capacitor, N-path and source-follower-based filters. The switched-capacitor and N-path filter types are not suitable in the case of a band-pass filter bank (as used e.g. in artificial cochlea systems) because the central frequency is dependent on the clock frequency, which is difficult to scale with a very small scaling ratio. The active RC type is also not suitable because, for a low central frequency (in the range of kHz and below), very large and thus area-consuming resistors and capacitors are required. The source-follower-based low-pass filter has been proven to be more power-efficient than the OTA-C low-pass filter, and therefore the source-follower-based topology has been chosen to construct the BPFs used in ultra-low-power silicon cochlea systems. Currently known source-follower-based BPFs have some limitations, as explained below. For example, some BPFs have a large pass-band gain loss when two or more same unit building blocks are cascaded for high-order filters. Some other BPFs have a band-pass transfer function which is highly sensitive to input common-mode voltage, while yet other BPFs are incapable of achieving high Q values, i.e. quality factors larger than 0.5. Furthermore, currently known cochlea systems have relatively high power consumption.

There is thus a need for a BPF that can be used in artificial cochlea systems for example and which does not have the drawbacks mentioned above.

SUMMARY OF THE INVENTION

According to a first aspect of the invention, there is provided a band-pass filter as recited in claim 1.

The proposed band-pass filter has a simple design, yet is stable and more power-efficient than many other filter topologies, such as active RC, gm-C etc. The proposed filter can be used in various applications, such as artificial cochlea systems, wireless transceivers, analogue-to-information converters etc.

According to a second aspect of the invention, there is provided a data processing apparatus comprising the band-pass filter according to the first aspect.

According to a third aspect of the invention, there is provided a method of operating the data processing apparatus according to the second aspect.

Other aspects of the invention are recited in the dependent claims attached hereto.

BRIEF DESCRIPTION OF THE DRAWINGS

Other features and advantages of the invention will become apparent from the following description of a non-limiting exemplary embodiment, with reference to the appended drawings, in which.

DETAILED DESCRIPTION OF AN EMBODIMENT OF THE INVENTION

Figure 1:
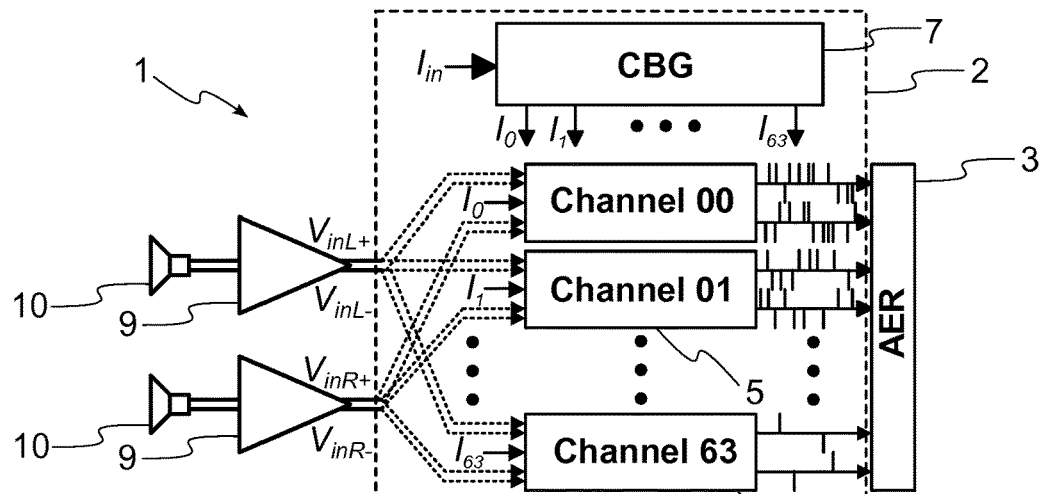
FIG. 1 is a simplified block diagram of a prior art artificial cochlea system.

An embodiment of the present invention will now be described in detail with reference to the attached figures. The invention will be described in the context of a silicon cochlea system. However, the teachings of the invention are not limited to use in artificial sensory systems, such as cochlea systems. The teachings of the present invention can also be applied to wireless transceivers, asynchronous data converters, other suitable clockless systems etc. Identical or corresponding functional and structural elements which appear in different drawings are assigned the same reference numerals.

Figure 2:
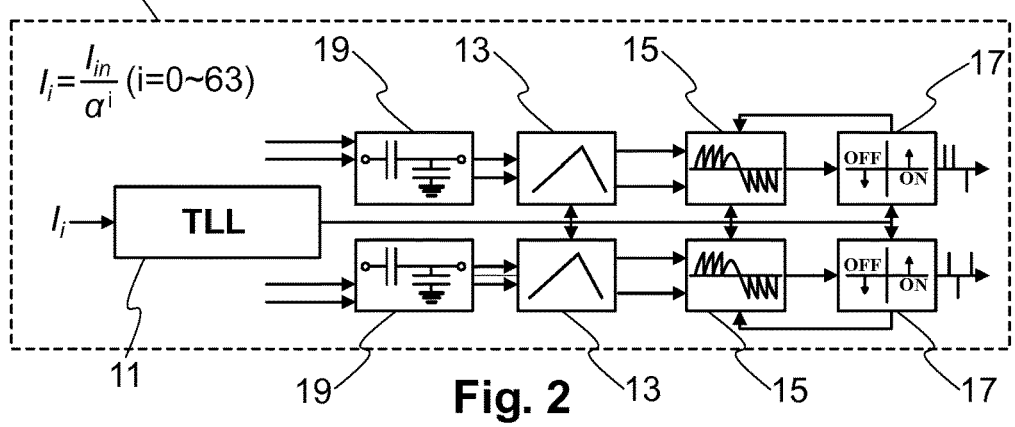
FIG. 2 is a simplified block diagram of one channel of the cochlea system of FIG. 1.
Figure 3:
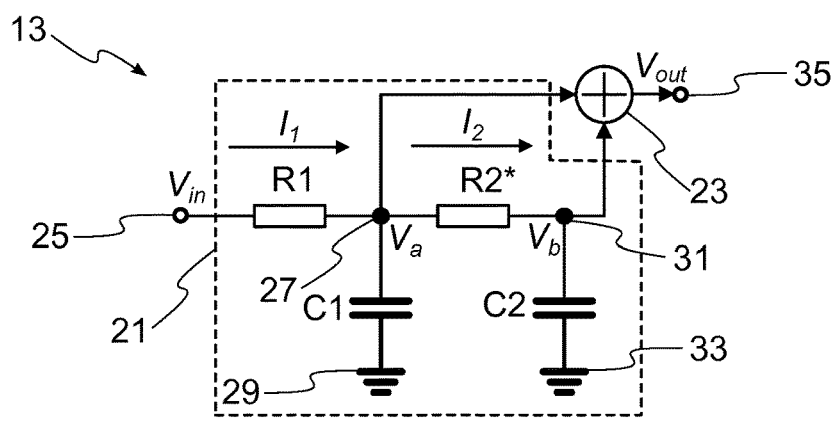
FIG. 3 is a circuit diagram of a band-pass filter according to an embodiment of the present invention.

FIG. 3 is a circuit diagram of a band-pass filter (BPF) 13 according to an embodiment of the present invention. This kind of BPF 13 may be used for example in the cochlea system of FIG. 1. More specifically, the proposed BPF 13 may be used to implement the filtering element 13 in FIG. 2. Turning back to FIG. 3, the proposed BPF 13 comprises a low-pass filter (LPF) 21 and summation means 23. The LPF 21 comprises a first first-order filter stage comprising a first resistor R1 characterised by a first impedance $R_1$. The first resistor R1 is connected to a first node 25, referred to as a filter input node, and, through a second node 27, to a first reactive component C1, in this example a first capacitor C1, characterised by a first capacitance $C_1$. The first capacitor C1 is connected to a third node 29, which in this example is directly connected to ground. The first resistor R1 is such that a first current $I_1$ through it (flowing from the first node 25 to the second node 27 in the diagram) is dependent on the difference between voltages at the first and second nodes:

$$I_1 = \frac{V_{in} - V_a}{R_1}, \quad (1)$$

where $V_{in}$ is the voltage value at the first node 25, while $V_a$ is the voltage value at the second node 27.

The LPF 21 also comprises a second first-order filter stage comprising a second resistor R2* characterised by a second impedance $R_2^*$ connected to the second node 27, and, through a fourth node 31, to a second reactive component C2, in this example a second capacitor C2 characterised by a second capacitance C2. The second capacitor C2 is connected to a fifth node 33. In this example the fifth node 33 is directly connected to ground. The second resistor R2* is such that a second current $I_2$ through it (from the second node 27 to the fourth node 31 in the diagram) is dependent on the negative of the sum of the voltages at the second and fourth nodes:

$$I_2 = -\frac{V_a + V_b}{R_2^*}, \quad (2)$$

where $V_b$ is the voltage at the fourth node 31.

It is to be noted that the second resistor R2* is not standard. The current flowing through the second impedance R2* is dependent on the sum of the input and output voltages, rather than on their difference, as in a standard ohmic impedance. The second impedance is a negative impedance. The first and second first-order filter stages together form the second order LPF 21.

As is shown in FIG. 3, the BPF 13 also comprises the summation means 23 for summing the voltages $V_a$, $V_b$ at second and fourth nodes 27, 31 to output a voltage at a sixth node 35. In this way a BPF can be obtained which has a simple structure and consumes very little power. As mentioned above, the proposed BPF 13 can for example be used in the cochlea system of FIG. 1. The band-pass transfer function of the RC circuit is $$\frac{V_{out}(s)}{V_{in}(s)} = \frac{\frac{C_2}{g_m}s}{\frac{C_1 C_2}{g_m^2}s^2 + \left(\frac{C_2}{g_{m2}} + \frac{C_1}{g_{m1}} - \frac{C_2}{g_{m1}}\right)s + 1}, \quad (3)$$

where $g_{m1}$ and $g_{m2}$ are the reciprocals, i.e. transconductances, of $R_1$ and $R_2^*$ respectively. The central frequency $f_0$ and the quality factor Q of the BPF 13 are expressed as $$f_0 = \frac{1}{2\pi}\sqrt{\frac{g_{m1} g_{m2}}{C_1 C_2}}, \quad Q = \frac{\sqrt{\frac{g_{m1} g_{m2}}{C_1 C_2}}}{\frac{g_{m1}}{C_1} + \frac{g_{m2}}{C_2} - \frac{g_{m2}}{C_1}} \quad (4)$$

Figure 4:
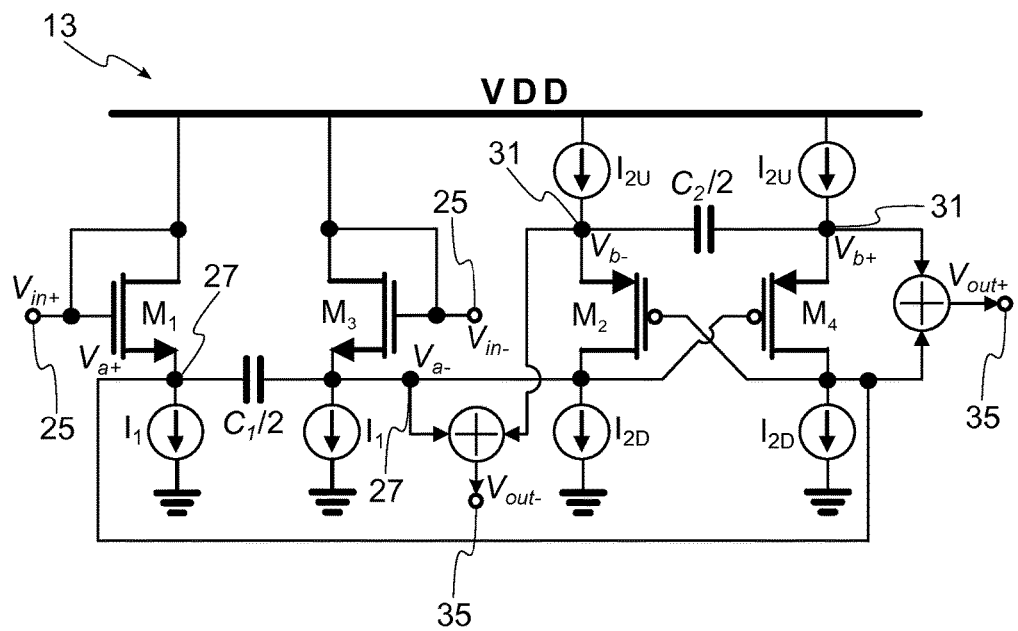
FIG. 4 is a circuit diagram of an implementation example of the circuit of FIG. 3.

The circuit diagram of FIG. 4 illustrates one exemplary implementation of the RC circuit of FIG. 3 by using a source-follower-based transistor circuit. As shown, this circuit illustration is a differential circuit. This means that there are two input nodes 25 so that the input signals at each of these nodes have a phase difference of 180 degrees. In the same manner there are two output nodes 35 so that the output signals at each of these nodes have a phase difference of 180 degrees. The illustrated circuit comprises four transistors, namely two n-type metal-oxide-semiconductor field-effect transistors (MOSFETs) M1, M3 and two p-type MOSFETs M2, M4. This exemplary circuit further comprises six current sources, of which two current sources $I_{2U}$ are directly connected to a power supply VDD, in this example a power rail, while four other current sources $I_1$, $I_{2D}$ are connected to ground. It is to be noted that the circuit illustrated in FIG. 4 is just one of many possible ways of implementing the RC circuit of FIG. 3.

Figure 5:
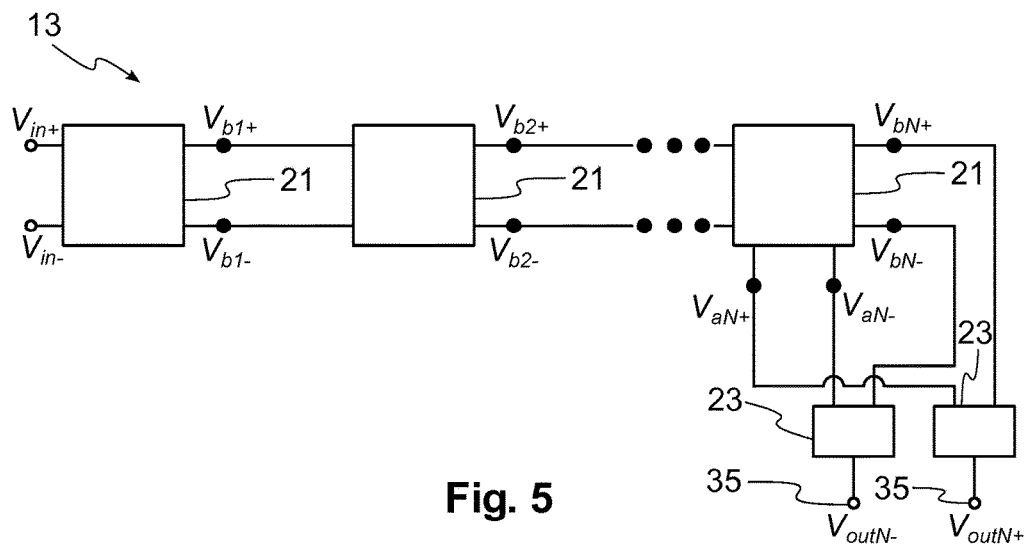
FIG. 5 is a circuit diagram of a band-pass filter where multiple filter stages are cascaded to form a higher order band-pass filter.
Figure 6:
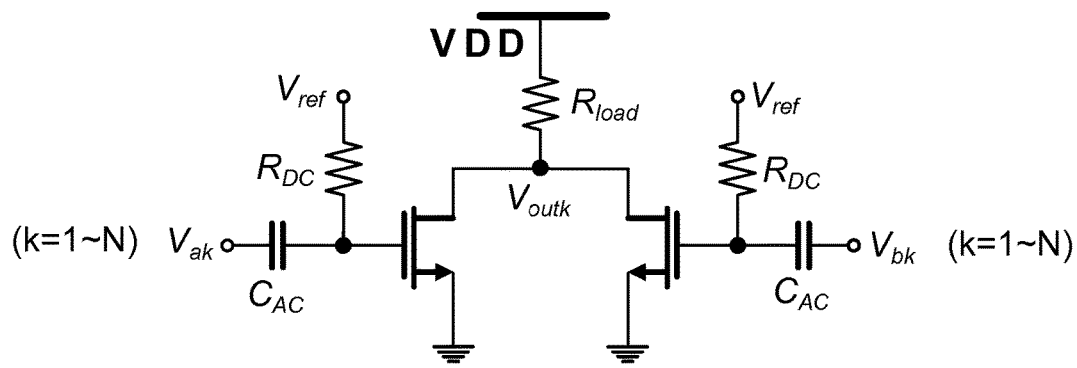
FIG. 6 is a circuit diagram of an exemplary summing circuit which can be used in the circuit of FIG. 5.

It is possible to cascade any number of the LPFs 21 to obtain a higher order LPF 21. For example, by cascading two of the LPFs shown in FIG. 3 or 4, a $4^{th}$ order LPF is obtained. A $4^{th}$ order asymmetrical BPF 13 is then obtained by summing $V_a$ and $V_b$ in the $2^{nd}$ LPF. FIG. 5 shows an example of the BPF 13, where N $2^{nd}$ order filter stages are cascaded. An exemplary summation circuit is illustrated in FIG. 6. This summation circuit can be used in the circuit illustrated in FIG. 5. It is to be noted that the summation means can be any suitable element arranged to perform a voltage summing operation. The summing means 23 could also be for instance a programmable gain amplifier (PGA), such as a capacitive adding amplifier with programmable gain. In this case a series of LPFs 21 would be cascaded and the PGAs' inputs would all come from the last filter stage. Thus, the BPF 13 would be composed of a series of N LPFs (e.g. source-follower-based) and a PGA.

Currently known source-follower-based low-pass and band-pass filters generally have very low quality factors Q, i.e. less than 2. A band-pass filter bank with large quality factors is useful for distinctive frequency-related feature extraction. For large quality factors, e.g. Q>10, the ratio of $C_2/C_1$ needs to be appropriately chosen to reduce variations in the central frequencies and quality factors between different BPFs 13. This is for example important for mitigating calibration overhead. It is to be noted that the variation of central frequency and Q can be compensated by manual calibration or on-chip automatic calibration with additional calibration circuits in the design. But in both cases, the calibration effort imposes extra labour or chip cost, and should therefore be avoided if possible. Thus, it is more cost-efficient to control the variation in the central frequency and Q by design rather than by calibration. Assuming $g_m$ is proportional to current in subthreshold operation of transistors, the method of determining the appropriate $C_2/C_1$ is summarised in the equation below:

$$\frac{Q + \sqrt{Q^2 + 4S_0^2 - 1}}{2S_0 + 1} \le n \le \sqrt{\frac{t_{ol}^2 + 2t_{ol}}{m_{is}}}, \quad (5)$$

where n is the square root of $g_{m2}/g_{m1}$, $t_{ol}$ is the relative variation of the central frequency $f_0$ (i.e. $f_0$ becomes $t_{ol}$% larger or $t_{ol}$% smaller) caused by $m_{is}$, which is the mismatch between the upper $I_{2U}$ and lower current sources $I_{2D}$ (i.e. the current value of $I_{2U}$ is $m_{is}$% larger or smaller than the current value of $I_{2D}$) (see FIG. 4 showing the upper and lower current sources) defining $R_2$*, and $S_0$ is the relative sensitivity of Q to $g_{m2}/g_{m1}$ (i.e. a 1% of variation in $g_{m2}/g_{m1}$ results in a $S_0$% variation in Q). The ratio $C_2/C_1$ can be calculated from the quality factor formula in (4) once n is determined according to (5).

The above BPF 13 according to an embodiment of the present invention was described in the context of the cochlea system. The proposed cochlea system enables a wide input dynamic range and consumes ultra-low power with a low supply voltage, making it possible to power the sensor with compact integrated energy harvesters. Next, further features of the present invention will be discussed, also in the context of the cochlea system.

Data converters, particularly analogue-to-digital or analogue-to-spike converters as used for example in cochlea systems can be divided into two categories: clocked and clockless. The industrial mainstream is currently the clocked type, and the clockless type is mostly still under research. Clockless converters have several advantages over clocked converters, such as a complete absence of aliasing without any anti-aliasing filters, input-activity-dependent power consumption in subsequent processing stages etc.

Both types of converters use comparators. In clocked converters, latched comparators are exclusively used nowadays instead of continuous-time comparators. Latched comparators normally use a regenerative latch with positive feedback, and require a clock signal to reset the latch after each comparison. Continuous-time comparators are normally open-loop, multi-stage amplifiers. Latched comparators are faster in comparison and more power-efficient than continuous-time comparators. However, in clockless converters, latched comparators are not readily used because of the lack of any clock. To date, the comparators used in clockless systems in literature all belong to the continuous-time type.

Figure 7:
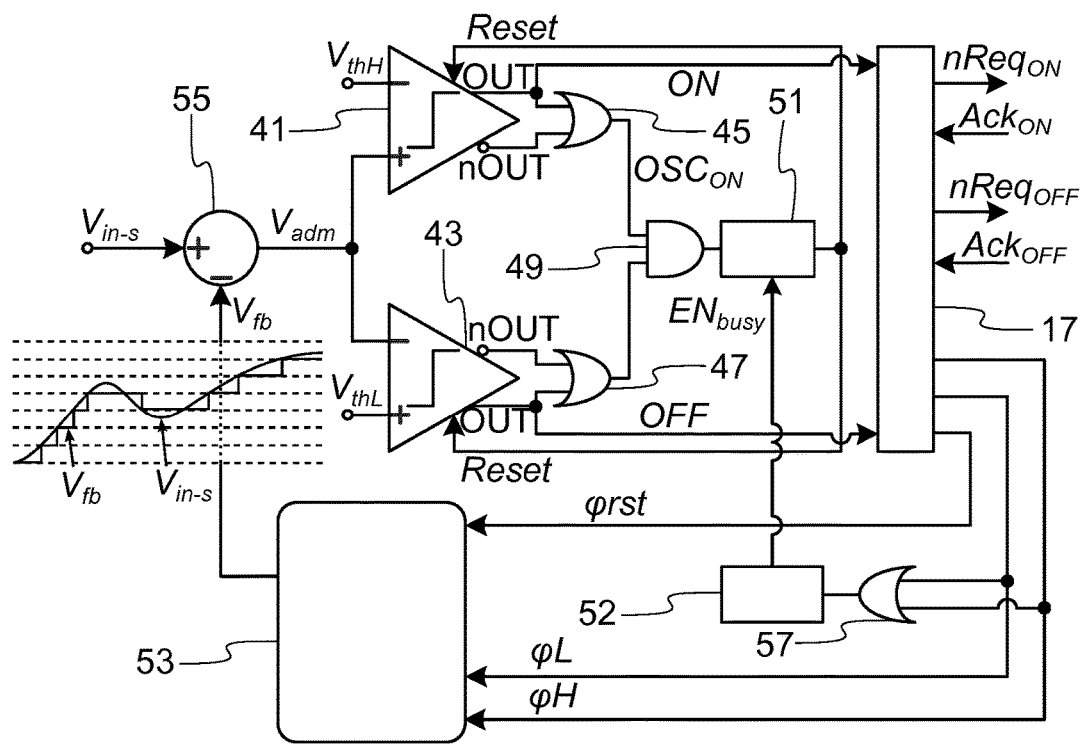
FIG. 7 is a circuit diagram of an exemplary asynchronous delta modulator, which can be used in the circuit of FIG. 2.
Figure 8:
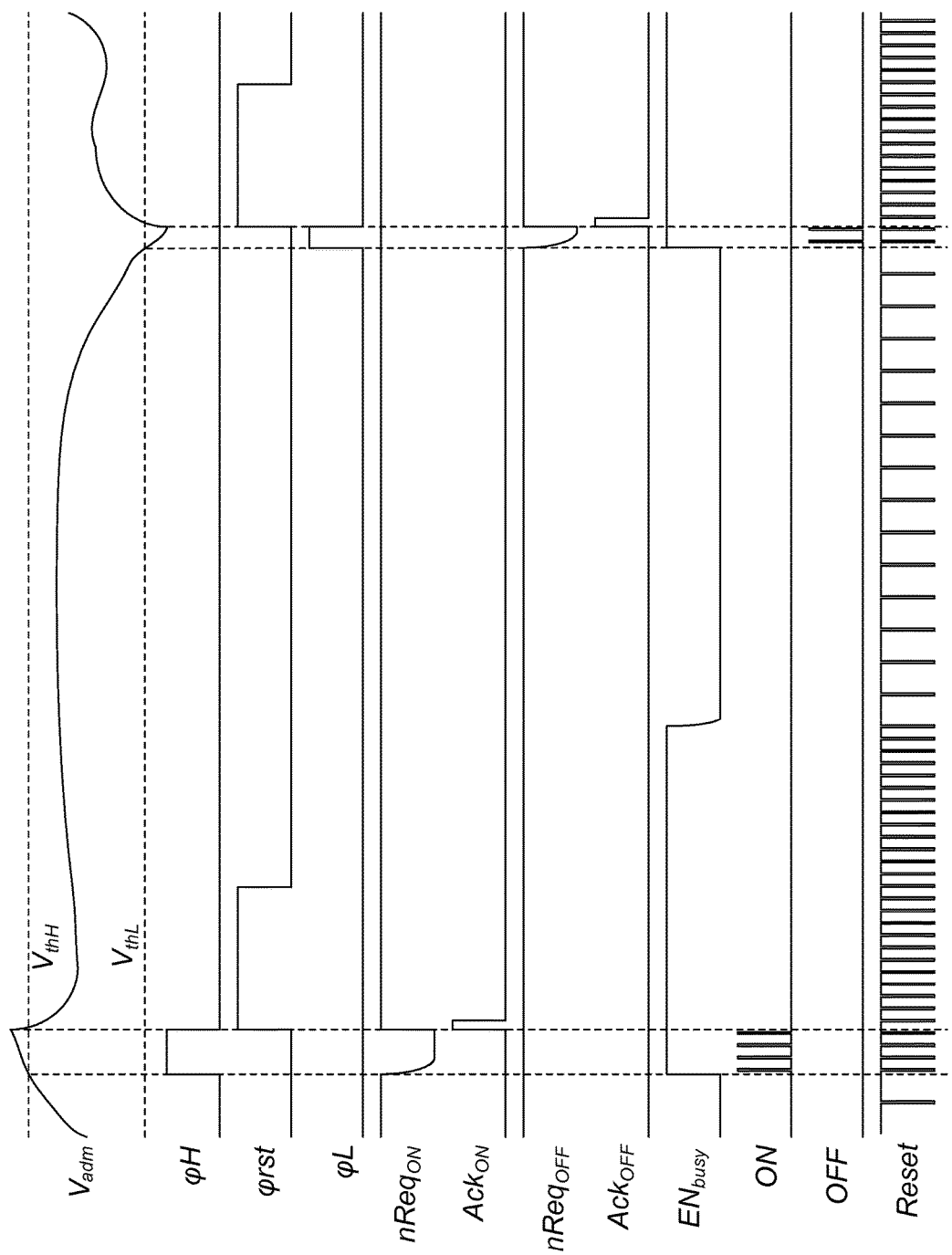
FIG. 8 is a time domain signal diagram showing some of the signals present in the circuit of FIG. 7.

According to the present invention, it is proposed to exploit the benefit of latched comparators in clockless converters by forming a self-oscillation loop to generate the pseudo-clock signal, and the frequency may be adaptive to the output rate of the converters. Taking the ADM 15, also referred to as a modulator circuit, as an example where two comparators are needed for comparison with an upper and a lower threshold voltage, the principle is illustrated in FIG. 7 and the exemplary timing diagram of some of the circuit signals is illustrated in FIG. 8. According to this example, the self-oscillation loop is formed by a first latched comparator 41, a second latched comparator 43, a first OR gate 45, a second OR gate 47, one AND gate 49, and one delay element 51. It is to be noted that the differential signal from the output of the BPF 13 is converted into the single-ended signal $V_{in-s}$ (see FIG. 7). $V_{fb}$ is the output of the integrator 53 as shown in FIG. 7. A subtraction element 55 gives at its output $V_{adm} = V_{in-s} - V_{fb}$. $V_{adm}$ can be regarded as the error signal between $V_{in-s}$ and $V_{fb}$. In other words, the feedback signal $V_{fb}$ tries to track the input signal $V_{in-s}$, and $V_{adm}$ indicates how far away $V_{fb}$ is from $V_{in-s}$. $V_{adm}$ is thus a modulated input signal of the ADM 15. $V_{fb}$ tracks $V_{in-s}$, and functionally the integrator 53 generates the tracking signal $V_{fb}$ through control signals φH, φL, and φrst so that the error signal $V_{adm}$ is ideally limited within an upper threshold $V_{thH}$ and a lower threshold $V_{thL}$. The latched comparators 41, 43 compare $V_{adm}$ with the upper threshold $V_{thH}$ and the lower threshold $Vt_{hL}$. Whenever $V_{adm}$ crosses above $V_{thH}$ or below $V_{thL}$, a spike is generated, and the asynchronous logic 17 controls the feedback which results in $V_{adm}$ being pulled back towards its DC level at 0.25 V, for example. This circuitry is one of several methods of implementing the ADM 15.

When $V_{adm}$ is below the upper threshold $V_{thH}$ and above the lower threshold $V_{thL}$, and the Reset is logic 0, i.e. invalid, the OUT terminals of the two comparators are logic 0, and the nOUT terminals are logic '1' after the completion of comparison. Therefore the outputs of the two OR gates 45, 47 are logic 1, and the output of the AND gate 49 is logic 1. After some delay, the Reset becomes logic 1, i.e. valid, both OUT and nOUT terminals of the two comparators become logic 0, and the output of the AND gate becomes logic 0. After some delay, the Reset becomes logic 0 again, and hence the self-oscillation is formed. When $V_{adm}$ goes above the upper threshold $V_{thH}$ and the Reset is logic 0, the OUT terminal of the ON comparator becomes logic 1, and the nOUT terminal becomes logic 0. The OUT terminal of the OFF comparator is still logic 0, and the nOUT terminal is still logic 1. The outputs of the two OR gates 45, 47 are still logic 1, and so is the AND gate output. The self-oscillation loop still works, and the self-oscillation loop also works in the case when $V_{adm}$ goes below the lower threshold $V_{thL}$.

To further save power, the time delay of the delay element 51 is controlled by the output activity of the two comparators 41, 43 and so the output of the BPF 13. Initially, when $V_{adm}$ is below $V_{thH}$ and above $V_{thL}$, both the signals ON and OFF stay at logic 0, and the control signals φH and φL are also logic 0. Therefore $EN_{busy}$ is logic 0, and the time delay of the delay element 51 is set to a larger value, so that the frequency of the self-oscillation is low. For latched comparators and logic gates, the power consumption is proportional to their operation frequency, therefore the power is further saved. Once $V_{adm}$ goes above $V_{thH}$ or below $V_{thL}$, ON or OFF becomes logic 1, and so does φH or φL. Logic 1 φH or φL sets $EN_{busy}$ to logic 1, and the time delay of the delay element is set to a smaller value, so that the frequency of the self-oscillation is high, to reduce the comparison delay and delay dispersion of spike generation. A timer circuit 52 starts to count time once φH or φL becomes logic 0 again. Once the time threshold of the timer 52 is crossed, $EN_{busy}$ goes back to logic 0, and the self-oscillation frequency becomes low again. So the timer circuit 52 is arranged to detect when the output activity (given by the frequency of the ON and OFF signals) is below a threshold, while the adjustment of the delay is implemented by the delay element 51. From the description above, the frequency of the self-oscillation loop is adaptively adjusted according to the activity level of the input to the ADM 15 (threshold crossing) for further power saving.

To better understand the signal timing, a detailed timing diagram is shown in FIG. 8. As shown in the timing diagram, once $V_{adm}$ goes above $V_{thH}$, a φH pulse is generated by the asynchronous logic 17 and sent to the integrator 53, and an $nReq_{ON}$ pulse is also generated by the asynchronous logic 17 and sent to an external receiver. After some time, an AckoN pulse is sent back to the asynchronous logic 17 from the external receiver, and triggers a φrst pulse. The consecutive φH and φrst pulses functionally increase $V_{fb}$ by δ, and cause $V_{adm}$ to be pulled below $V_{thH}$. The signal flow of an OFF event when $V_{adm}$ goes below $V_{thL}$ is similar. $EN_{busy}$ stays at logic 0 when $V_{adm}$ is below $V_{thH}$ and above $V_{thL}$, and consequently the oscillation frequency of the Reset signal is low. Once φH or φL becomes logic 1, $EN_{busy}$ becomes logic 1 which is enabled by a third logic OR gate 57 in front of the timer 52, and consequently the self-oscillation frequency of the Reset signal becomes high. Once φH or φL goes back to logic 0 again, the timer 52 starts to count time. Once the time threshold of the timer 52 is crossed, $EN_{busy}$ is set back to logic 0 again, and the self-oscillation frequency of the Reset signal becomes low again.

It is of course possible to have one dynamic latched comparator with the self-oscillating loop so that a signal is compared to one threshold only, i.e. either $V_{thH}$ or $V_{thL}$ using the above example. In that case, the circuit described above would be simplified so that the second comparator 43, the second OR gate 47 and the AND gate 49 could be omitted. In that case, the output of the first OR gate 45 would be directly connected to the delay element 51. Moreover, it is to be noted that the described latched comparators in a self-oscillating loop and the method of power reduction via dynamic adaptation of the self-oscillation frequency are not confined to the ADM 15 described here. It is suitable for any clockless system that needs comparison. For example, it can be easily integrated into clockless level-crossing analogue-to-digital converters.

While the invention has been illustrated and described in detail in the drawings and foregoing description, such illustration and description are to be considered illustrative or exemplary and not restrictive, the invention being not limited to the disclosed embodiment. Other embodiments and variants are understood, and can be achieved by those skilled in the art when carrying out the claimed invention, based on a study of the drawings, the disclosure and the appended claims.

In the claims, the word "comprising" does not exclude other elements or steps, and the indefinite article "a" or "an" does not exclude a plurality. The mere fact that different features are recited in mutually different dependent claims does not indicate that a combination of these features cannot be advantageously used. Any reference signs in the claims should not be construed as limiting the scope of the invention.

The invention claimed is:

1. A band-pass filter comprising:
    a first first-order filter stage comprising a first resistor characterised by a first impedance and connected to a first node, referred to as a filter input node, and, through a second node, to a first reactive component connected to a third node, the first impedance being such that a first current therethrough is dependent on the difference between the voltages at the first and second nodes when the first current flows from the first node to the second node;
    a second first-order filter stage comprising a second resistor characterised by a second impedance and connected to the second node, and, through a fourth node, to a second reactive component connected to a fifth node, the second impedance being such that a second current therethrough is dependent on the negative of the sum of the voltages at the second and fourth nodes when the second current flows from the second node to the fourth node; and
    a summing element for summing the voltages at the second and fourth nodes to output a voltage at a sixth node.

2. A band-pass filter according to claim 1, wherein the first and second first-order filter stages comprise a first first-order low-pass filter and a second first-order low-pass filter respectively.

3. A band-pass filter according to claim 2, wherein the first and second first-order low-pass filters each comprise a source-follower-based transistor circuit.

4. A band-pass filter according to claim 1, wherein the first current is given by:

$$I_1 = \frac{V_{in} - V_a}{R_1},$$

where $I_1$ is the first current, $V_{in}$ is the voltage at the first node, $V_a$ is the voltage at the second node, and $R_1$ is the first impedance, and wherein the second current is given by:

$$I_2 = -\frac{V_a + V_b}{R_2^*},$$

where $I_2$ is the second current, $V_b$ is the voltage at the fourth node, and $R_2^*$ is the second impedance.

5. A band-pass filter according to claim 1, wherein the summing element comprises a summing amplifier.

6. A band-pass filter according to claim 1, wherein the first and second reactive components are capacitors.

7. A band-pass filter according to claim 6, wherein the first and second capacitances are such that the following conditions are fulfilled:

$$Q = \frac{\sqrt{\frac{g_{m1}g_{m2}}{C_1 C_2}}}{\frac{g_{m1}}{C_1} + \frac{g_{m2}}{C_2} - \frac{g_{m2}}{C_1}},$$

where Q is a quality factor of the band-pass filter, $C_1$ is a capacitance value of the first capacitor, $C_2$ is a capacitance value of the second capacitor, $g_{m1}$ is a reciprocal of the first impedance, and $g_{m2}$ is a reciprocal of the second impedance; and $$\frac{Q + \sqrt{Q^2 + 4S_0^2 - 1}}{2S_0 + 1} \le n \le \sqrt{\frac{t_{ol}^2 + 2t_{ol}}{m_{is}}},$$

where n is a square root of $g_{m2}/g_{m1}$, $t_{ol}$ is the relative variation of the band-pass filter central frequency $f_0$ caused by $m_{is}$, which is mismatch between currents in first and second current sources connected to first sides of transistors and second sides of the transistors, respectively, of a transistor circuit implementation of the band-pass filter, and $S_0$ is the relative sensitivity of Q to $g_{m2}/g_{m1}$.

8. A band-pass filter according to claim 1, wherein more than one second-order filter stages, each comprising the first first-order filter stage and the second first-order filter stage, are cascaded to form a higher order band-pass filter.

9. A data processing apparatus comprising two or more of the band-pass filters according to claim 1.

10. A data processing apparatus according to claim 9, wherein the data processing apparatus comprises a clockless modulator circuit comprising a latched comparator and comprising a self-oscillating loop for generating a pseudo-clock signal for the modulator circuit.

11. A data processing apparatus according to claim 10, wherein the self-oscillation loop comprises a first comparator, a first logic gate connected to an output of the first comparator for detecting completion of the comparison, and a delay element connected to the first logic gate, the delay element being connected to the first comparator by a first feedback loop for providing a reset signal for the first comparator.

12. A data processing apparatus according to claim 11, wherein the self-oscillation loop further comprises a second comparator, a second logic gate connected to an output of the second comparator for detecting completion of the comparison, and to an AND gate located between the first logic gates and the delay element, the delay element being further connected to the second comparator by a second feedback loop for providing a reset signal for the second comparator.

13. A data processing apparatus according to claim 10, wherein the frequency of the pseudo-clock signal is arranged to be dependent on an input signal activity of the modulator circuit.

14. A data processing apparatus according to claim 9, wherein the processing apparatus comprises an artificial cochlea system or an analogue-to-digital converter.

15. A method of operating the data processing apparatus according to claim 10, the method comprising:
   determining a signal level of a modulated input signal of the modulator circuit;
   increasing the frequency of the pseudo-clock signal if the signal level exceeds a first threshold or goes below a second threshold; and
   decreasing the frequency of the pseudo-clock signal if the signal level is between the first and the second thresholds, wherein the frequency is decreased once a time period given by a timer circuit has lapsed after detection of the signal level between the first and the second thresholds.

* * * * *